United States Patent [19]

Wolgemuth

[11] 4,395,392

[45] Jul. 26, 1983

[54] METHOD FOR TREATING KIDNEY STONES

[75] Inventor: Richard L. Wolgemuth, Plain City, Ohio

[73] Assignee: Adria Laboratories Inc., Columbus, Ohio

[21] Appl. No.: 278,014

[22] Filed: Jun. 29, 1981

Related U.S. Application Data

[63] Continuation-in-part of Ser. No. 162,477, Jun. 24, 1980, abandoned.

[51] Int. Cl.$^3$ ............................................. A61K 31/795
[52] U.S. Cl. .......................................... 424/78; 424/79
[58] Field of Search ...................................... 424/78, 79

[56] References Cited

U.S. PATENT DOCUMENTS 3,893,890  7/1975  Wurzburg et al. .................... 424/78
3,961,045  6/1976  Wurzburg et al. .................... 424/78
4,143,130  3/1979  Imondi et al. ..................... 424/79 X

FOREIGN PATENT DOCUMENTS 1498101  1/1978  United Kingdom .

OTHER PUBLICATIONS

Burghele et al., Der Urologe, 1967, pp. 234–238.
Pak et al., 290 (4), 175–180, Jan. '74.

*Primary Examiner*—Albert T. Meyers
*Assistant Examiner*—John W. Rollins
*Attorney, Agent, or Firm*—Marion C. Staves

[57] ABSTRACT

A method for decreasing urinary calcium content which comprises orally administering to a person whose urine contains insoluble calcium containing precipitates or has a propensity for forming calcium containing precipitates, an effective amount of an agent selected from water-soluble vinylbenzenesulfonic acid polymers and the nontoxic pharmaceutically acceptable salts thereof.

2 Claims, No Drawings

METHOD FOR TREATING KIDNEY STONES

This application is a continuation-in-part of co-pending application Ser. No. 162,477, filed June 24, 1980 now abandoned.

BACKGROUND OF THE INVENTION

1. Field of the Invention

This invention relates to methods and compositions for treating kidney stones. More particularly, this invention relates to compositions containing water-soluble vinylbenzenesulfonic acid polymers and their use in treating kidney stones.

2. Description of the Prior Art

In the United States alone, there are each year about 250,000 newly diagnosed patients with kidney stones. Analysis of these stones shows that 70% of all kidney calculi contain calcium. Successful treatment of calcium containing kidney calculi occurs with the reduction of urinary calcium excretion. Urinary calcium excretion can be lowered by the oral administration of a calcium sequestrant which binds calcium in the gastrointestinal tract. In essence, by increasing the fecal calcium load, calcium sequestrants decrease the calcium load on the kidney.

The binding and removal of calcium by highly cross-linked carboxylic resins is known and has been used in the removal of calcium from water and blood. In 1968, Burghele et al. (*Urologe*, 6:234 (1968)) introduced the use of highly cross-linked insoluble resins as a means of kidney stone prophylaxis. See also, Pak et al. (*New England J. Med.*, 290:4, 1974), Successful Treatment of Recurrent Nephrolithiasis (Calcium Stones) with Cellulose Phosphate, and British Pat. No. 1,498,101, Drugs for Use in the Prevention and Treatment of Lithiasis. Water-soluble and swellable carboxylic acid polymers which are calcium sequestrants are disclosed in U.S. Pat. No. 4,143,130.

The water-soluble vinylbenzenesulfonic acid polymers used in this invention are known products of commerce sold by the National Starch and Chemical Corporation and are disclosed as useful for treating ulcers and inhibiting the action of pepsin in U.S. Pat. Nos. 3,961,045 and 3,893,890.

SUMMARY OF THE INVENTION

It has now surprisingly been discovered that certain water-soluble polymers of vinylbenzenesulfonic acids are useful for decreasing urinary calcium content and are more effective and less toxic than the prior art compositions. Accordingly, this invention relates to a treatment for decreasing urinary calcium content which comprises orally administering to a person in need of such treatment a therapeutically effective amount of an agent selected from water-soluble vinylbenzenesulfonic acid polymers and their nontoxic pharmaceutically acceptable salts.

The agents useful in this invention are water-soluble polymers having a molar degree of sulfonation of at least 70%, most preferably from about 70 to over 90% molar monosulfonation said polymers having repeating units of the following structural formula:

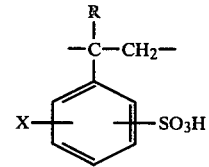

where R is hydrogen or methyl and X is hydrogen, halogen or lower alkyl (i.e., 1–5 carbons), the polymer having a viscosity average molecular weight in the range of from about 20,000 to about 1,000,000, most preferably from about 50,000 to about 500,000, wherein said polymers contain less than 5%, based on total weight, of polymers having a molecular weight of less than 20,000. In general, the homopolymers of vinylbenzenesulfonic acids are most useful. However, it may be desirable in certain cases to copolymerize the vinylbenzenesulfonates with monomers to introduce into the polymer no more than 30 mole % of repeating units of the following formula:

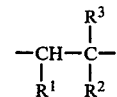

where $R^1$ and $R^2$ are the same or different radicals selected from hydrogen or lower alkyl radicals; $R^3$ is a radical selected from acyloxy radicals, for example, alkanoyloxy such as acetoxy, propionyloxy, butyryloxy and the like, or benzoyloxy; lower alkoxy radicals such as methoxy, ethoxy and the lick, and phenyl radicals.

The polymers may be synthesized by any conventional method, for example, bulk, suspension, solution or emulsion polymerization methods, and the sulfonation may be carried out according to the method taught in U.S. Pat. No. 3,072,618. It will be obvious to those skilled in the art that the polymers may have different end groups depending on the method they were made. For example, polymers made by emulsion polymerization may have —OH, —COOH or —SO$_4$H on one end and —H on the other. Polymers made by bulk polymerization using an organic peroxide initiator may have ester or ether groups on one end and —H on the other. It will be understood that the term "water-soluble vinylbenzenesulfonic acid polymers" appearing in the specification and claims means polymers having such end groups. Those skilled in the art will recognize that the end groups constitute only an infinitesimal amount of the total polymer and are nontoxic and inert with respect to the claimed treatment.

The polymeric agents used in this invention are not absorbed systemically into the circulating lumph or blood. Thus, the orally administered polymers are entirely excreted in the feces. There is no absorbed polymer in any of the tissues or organs of the treated host. The polymers cause no caecal ulceration in the normal guinea pig and no gastrointestinal irritation or toxicity in rats or dogs when fed at doses as high as two grams per kilo for 30 days or more. Lower molecular weight polymers (i.e., polymers having a molecular weight below 20,000), such as the polymers disclosed in U.S. Pat. Nos. 3,961,045 and 3,893,890, cause physiological reactions in guinea pigs and dogs, including extreme irritation and toxicity. This discovery of toxicity due to the presence of polymers having a molecular weight below about 20,000 forms a basis for the selection of the preferred class of polymers used in this invention.

In general, the polymers will be used in the form of their salts. Typical nontoxic pharmaceutically acceptable salts useful in this invention are the sodium, potassium, ammonium and amine salts.

The compositions containing the sulfonic acid-containing polymers or their salts can be administered in a wide variety of therapeutic dosages and in a wide variety of pharmaceutically acceptable carriers. Typical formulations contain from about 10% to about 20% of the product in a suitably flavored, colored, preserved, aqueous mixture. Typical unit dosages will vary from about 0.7 g to about 21 g. The liquid dosage form may contain, in addition to water, small amounts of ethanol or other pharmaceutically acceptable solvent or solvents. Other dosages forms include gels prepared with pectin, agar, hydroxyethyl cellulose or other approved gelling agents, tablets, capsules and pills, which may be microencapsulated, or enterically coated.

In addition, formulations may contain combinations of additional drugs particularly suited to the treatment of kidney stones and relief of pain. Other oral drug combinations are also within the scope of this invention.

The oral daily dosage of the products may be varied over a wide range varying from about 10 mg to about 400 mg/kg/day, which may be subdivided into three or four doses per day. The product can be administered in subdivided doses in the form of scored tablets or capsules; however, for the disclosed polymers, liquid dosage forms are preferred. The dosage forms permit the symptomatic adjustment of the dosage to the patient to be treated.

The following examples are illustrative of how to prepare various compositions containing the active ingredients of this invention. However, said examples are merely illustrative and should not be construed as limiting the scope of this invention.

EXAMPLE A-Tablets Containing 500 mg of Active Ingredients per Tablet

|  | Per Tablet |
| --- | --- |
| Polystyrene Sulfonic Acid MW = 70,000 | 500 mg |
| Sodium Phosphate Dibasic | 73 mg |
| Lactose | 70 mg |
| Corn Starch | 50 mg |
| Magnesium Stearate | 7 mg |

Weigh and pass each ingredient through a No. 10 mesh screen (U.S. Sieve). Blend the ingredients in a twin-shell blender for 10 minutes. Compress tablets to a weight of 700 mg per tablet on a tablet machine.

EXAMPLE B-Oral Elixir Dosage Form Containing 500 mg of Active Ingredient per Five ml.

|  | Per 5 ml. |
| --- | --- |
| Na Polystyrene Sulfonic Acid MW = 300,000 | 750 mg |
| Sorbitol Solution 70% W/W | 1000 mg |
| Ethyl Alcohol | 500 mg |
| Propylparaben | 5 mg |
| FD & C Yellow No. 5 | 0.2 mg |
| Flavoring Agent | 0.03 mg |
| Purified Water | qs |

The polystyrenesulfonic acid is dissolved in a portion of water by gentle agitation. The sorbitol is added to this solution. The FD & C No. 5 is dissolved in a portion of water and added to the above solution. The propylparaben is dissolved in a portion of ethyl alcohol. The flavoring agent is dissolved in the remaining ethyl alcohol. The two ethanolic solutions are then added to the aqueous solution above. Sufficient water is then added to bring to a final volume with continuous agitation.

The following examples illustrative the products of this invention and the process for preparing them. Parts and percentages are by weight unless indicated otherwise.

EXAMPLE 1

This example illustrates the use of polystyrenesulfonate having a molecular weight of 70,000 (manufactured by National Starch Corporation). One hundred and fifty ml. of the polymer was neutralized to pH 6.5 with 1 N sodium hydroxide. The polymer was freeze dried, ground and added to ground rat chow until the final concentration of the test material was 2.5%. A control substance was prepared exactly the same by substituting microcrystalline cellulose for the polystyrenesulfonate. The test animals were female Sprague Dawley rats. Eight rats were used per test. Urine was collected for 6 hours on the fifth day of treatment and analyzed for calcium by Precision Systems Automatic Calcium Analyzer. The results are tabulated in Table 1.

TABLE 1

| Effect of Soluble Sodium Polystyrenesulfonic Acid on Urinary Calcium Excretion in the Laboratory Rat | |
| --- | --- |
| Test Substance | Urinary Calcium[1] Micromoles/6h |
| Control (microcrystalline cellulose) | 358 ± 76 |
| Product of this Invention - Soluble Polystyrenesulfonate | 127 ± 42 |

[1]Data presented are mean ± 1 SEM

The results show that when compared to microcrystalline cellulose (the control) polystyrenesulfonic acid causes a significant decrease in urinary calcium.

EXAMPLE 2

This example compares the toxicity of soluble polystyrenesulfonic acid, PSS, (MW 70,000) with soluble polyacrylic acid, PAA, (MW 70,000). Both materials were neutralized to pH 7.1 with potassium hydroxide. Final concentration of each polymer was 15%. Sixty-six female Sprague Dawley rats were divided into eleven groups with six rats per group. Each rat was gavaged with a single dose of one of the two polymers in an amount shown in Table 2. Mortality was determined in each test group each day for three days. Seventy-two hour survival for both compounds is shown below.

TABLE 2

| Acute Toxicity of Soluble Polystyrenesulfonate (PSS) and Polyacrylic Acid (PAA) in the Potassium Form | | | |
| --- | --- | --- | --- |
| Group | Treatment[1] (mpk) | Body Wt. (g)[2] | 72 hour Survival |
| A | 0 | 193 ± 16 | 6/6 |

TABLE 2-continued

Acute Toxicity of Soluble Polystyrenesulfonate (PSS) and Polyacrylic Acid (PAA) in the Potassium Form

| Group | Treatment[1] (mpk) | Body Wt. (g)[2] | 72 hour Survival |
|---|---|---|---|
| B | 1500 PAA | 198 ± 12 | 6/6 |
| C | 2250 PAA | 183 ± 7 | 1/6 |
| D | 3000 PAA | 195 ± 10 | 0/6 |
| E | 3750 PAA | 186 ± 7 | 0/6 |
| F | 4500 PAA | 193 ± 9 | 0/6 |
| H | 1500 PSS | 194 ± 11 | 6/6 |
| I | 2250 PSS | 184 ± 10 | 6/6 |
| J | 3000 PSS | 183 ± 16 | 6/6 |
| K | 3750 PSS | 192 ± 5 | 6/6 |
| L | 4500 PSS | 190 ± 6 | 6/6 |

[1]Acid form of polymers neutralized to pH 7.1 with potassium hydroxide. Final concentration of polymer is 15%.
[2]Data presented are mean ± SD.

What I claim and desire to protect by Letters Patent is:

1. A treatment for decreasing urinary calcium content which comprises orally administering to a host in need of such treatment, a therapeutically effective amount of an agent selected from water-soluble vinylbenzenesulfonic acid polymers having a viscosity average molecular weight in the range of from about 50,000 to about 500,000 and containing less than 5% by weight of polymers having a molecular weight of less than 20,000, wherein the polymers have from about 70 to over 90% molar monosulfonation and the nontoxic pharmaceutically acceptable salts thereof.

2. A treatment for decreasing urinary calcium content which comprises orally administering to a hose in need of such treatment, a therapeutically effective amount of a vinylbenzenesulfonic acid homopolymer having a viscosity average molecular weight range of from about 50,000 to about 500,000 and containing less than 5% by weight of polymers having a molecular weight of less than 20,000, having repeating units of the formula

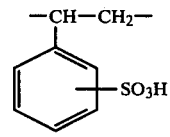

wherein the polymer has from about 70 to over 90% molar monosulfonation and nontoxic pharmaceutically acceptable salts thereof.

* * * * *

UNITED STATES PATENT AND TRADEMARK OFFICE
CERTIFICATE OF CORRECTION

PATENT NO. : 4,395,392
DATED : July 26, 1983
INVENTOR(S) : Richard L. Wolgmuth

It is certified that error appears in the above-identified patent and that said Letters Patent are hereby corrected as shown below:

Column 2, line 35 " lick " should read -- like --;

Column 2, line 56 " lumph " should read -- lymph --;

Column 4, line 15 " illustrative " should read -- illustrate --; and

In the Claims, Column 6, line 7 " hose " should read -- host --.

Signed and Sealed this

Eleventh Day of October 1983

[SEAL]

Attest:

Attesting Officer

GERALD J. MOSSINGHOFF

Commissioner of Patents and Trademarks